(12) United States Patent
Dierynck et al.

(10) Patent No.: US 6,800,437 B1
(45) Date of Patent: Oct. 5, 2004

(54) METHOD OF MONITORING A BIOLOGICAL SYSTEM BY LABELING WITH AN APO METAL BINDING PROTEIN

(75) Inventors: Inge Dierynck, Wilrijk (BE); Christiaan Hubert Simon Roelant, Leuven (BE); Rudi Wilfried Jan Pauwels, Bonheiden (BE); Koenraad Lodewijk August Van Acker, Temso (BE); Jan Octaaf Antoon De Kerpel, Lede (BE)

(73) Assignee: Tibotec Bvba, Mechelen (BE)

( * ) Notice: Subject to any disclaimer, the term of this patent is extended or adjusted under 35 U.S.C. 154(b) by 279 days.

(21) Appl. No.: 09/633,232

(22) Filed: Aug. 4, 2000

Related U.S. Application Data

(60) Provisional application No. 60/147,339, filed on Aug. 6, 1999.

(51) Int. Cl.$^7$ ................................................. C12Q 1/68
(52) U.S. Cl. ........................................................... 435/6
(58) Field of Search .......................... 435/4, 6, 7.1, 7.2

(56) References Cited

U.S. PATENT DOCUMENTS

| | | | |
|---|---|---|---|
| 5,491,084 A | | 2/1996 | Chalfie et al. |
| 5,612,016 A | * | 3/1997 | Griffiths et al. ............ 424/1.49 |
| 5,985,215 A | | 11/1999 | Sakazume et al. |
| 6,046,056 A | | 4/2000 | Parce et al. |

FOREIGN PATENT DOCUMENTS

| | | |
|---|---|---|
| WO | WO 97/27480 | 7/1997 |
| WO | WO 99/30154 | 6/1999 |
| WO | WO 99/67639 | 12/1999 |
| WO | WO 00/14540 | 3/2000 |

OTHER PUBLICATIONS

Cormack et al., "FACS–optimized Mutants of the Green Fluorescent Protein (GFP)," *Gene*, vol. 173 pp., 33–38 (1996).

Garrett et al., "The Crystal Structure of Poplar Apoplastocyanin at 1.8–Å Resolution," *The Journal of Biological Chemistry*, vol. 259, No. 4, pp. 2822–2825 (1984).

Garrett et al., "Type–1 Copper (Blue) Proteins Signature," http://bess.u–strasbg.fr/BioInfo/Proste/00174.pdoc (Last Update: 1995).

Holm et al., "Structural and Functional Aspects of Metal Sites in Biology," *Chem. Rev.*, vol. 96, pp. 2239–2314 (1996).

Kroes et al., The Mutation Met121→His Creates a Type–1.5 Copper Site in *Alcaligenes Denitrificans* Azurin, *Eur. J. Biochem.*, vol. 240, pp. 342–351 (1996).

Mann et al., "The Amino Acid Sequence of a Type I Copper Protein with an Unusual Serine– and Hydroxyproline–rich C–Terminal Domain Isolated From Cucumber Peelings," *FEBS Letters*, vol. 314, No. 3, pp. 220–223 (1992).

Mattar et al., "The Primary Structure of Halocyanin, an Archael Blue Copper Protein, Predicts a Lipid Anchor for Membrane Fixation," *The Journal of Biological Chemistry*, vol. 269, No. 21, pp. 14939–14945 (1994).

McManus et al., "Isolation, Characterization, and Amino Acid Sequences of Auracyanins, Blue Copper Proteins from the Green Photosynthetic Bacterium *Chloroflexus aurantiacus*," *The Journal of Biological Chemistry*, vol. 267, No. 10, pp. 6531–6540 (1992).

Gordon et al., "Lux Genes and the Applications of Bacterial Bioluminescence," *Journal of General Microbiology*, vol. 138, pp. 1289–1300 (1992).

Gould et al., "Firefly Luciferase as a Tool in Molecular and Cell Biology," *Analytical Biochemistry*, vol. 175, pp. 5–13 (1988).

Rydén et al., "Evolution of Protein Complexity: The Blue COpper–Containing Oxidases and Related Proteins," *J. Mol. Evol.*, vol. 36, pp. 41–66 (1993).

Silhavy et al., "Uses of Lac Fusions for the Study of Biological Problems," *Microbiological Reviews*, vol. 49, No. 4, pp. 398–418 (1985).

Yano et al., "The Amino Acid Sequence of Rusticyanin Isolated from *Thiobacillus Ferrooxidans*," *FEBS Letters*, vol. 288, No. 1, 2, pp. 159–162 (1991).

* cited by examiner

*Primary Examiner*—Terry McKelvey
(74) *Attorney, Agent, or Firm*—Woodcock Washburn LLP

(57) ABSTRACT

The present invention is directed to reporter molecules and tags that may be used to monitor a target substance in a biological system. More particularly, the present invention relates to the use of an apo metal binding protein as a reporter molecule or tag. An apo metal binding protein may be bound to a protein or tissue or introduced into a cell. The invention also relates to methods of utilizing the apo metal binding protein for detecting a cell expressing a protein of interest, localizing a protein in a cell, and designing a therapeutic agent for treating a disease or infection.

6 Claims, 4 Drawing Sheets

Figure 1

Primer design

*5' primer BCP-1C:*

5'- gac aga <u>agc ttc</u> gcc acc <u>atg ctg gca aaa gcc ac</u> -3'   (SEQ ID:1)
      < *Hind*III >         <     *azu* gene     >
            < Kozak >

*3' primer BCP-1NC:*

5'- gac aga <u>att cag</u> <u>ttg ctc agc ttg agc gtg</u> -3'   (SEQ ID:2)
      < *Eco*RI >  <    *azu* gene    >
          < * >

*5' primer BCP-2C:*

5'- gac aga <u>agc ttc</u> gcc acc <u>atg gag aca gac aca ctc ctg cta tgg gta ctg ctc</u>
      < *Hind*III >      <         Igκ-leader sequence
           < Kozak >

<u>tgg gtt cca ggt tcc act ggt gac</u> atg ctg gca aaa gcc ac -3'   (SEQ ID:3)
                       > <  *azu* gene  > pLNCX-BCP1 vector information

Figure 3
Blot 1: BCP1 (sample 1), antibody: anti A. denitrificans azurine
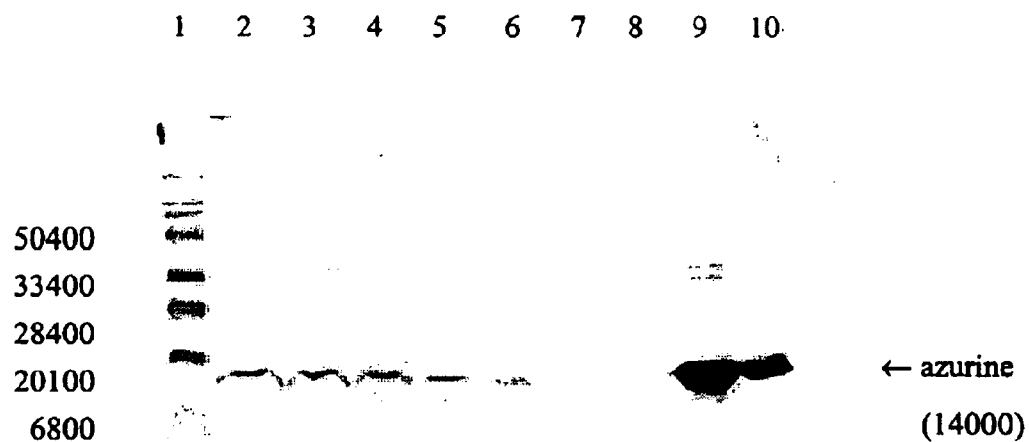
Blot 2: BCP1 (sample 2), antibody: anti P. aeruginosa azurine
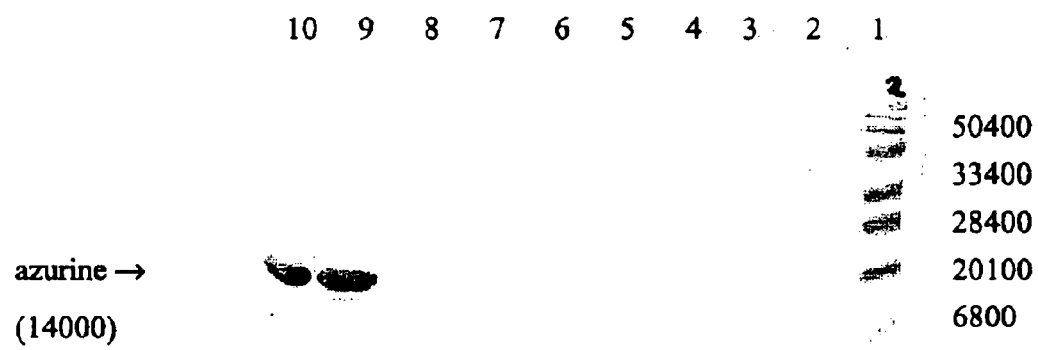

Figure 3 (Con't)
Blot 3: BCP2 (sample 3), antibody: anti A. denitrificans azurine
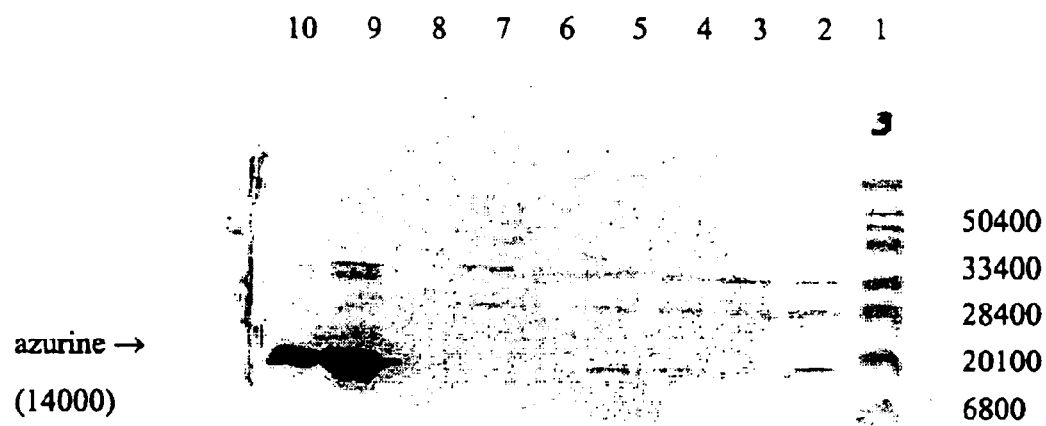
Blot 4: BCP2 (sample 4), antibody: anti P. aeruginosa azurine

METHOD OF MONITORING A BIOLOGICAL SYSTEM BY LABELING WITH AN APO METAL BINDING PROTEIN

This application claims the benefit of U.S. provisional application Ser. No. 60/147,339, filed Aug. 6, 1999, which is hereby incorporated by reference in its entirety.

The present invention is directed to the field of reporter molecules and tags that may be used to monitor a target substance in a biological system. More particularly, the present invention relates to the use of an apo metal binding protein as a reporter molecule or tag. An apo metal binding protein may be bound to a protein or tissue or introduced into a cell. The invention also relates to methods of utilizing the apo metal binding protein for detecting a cell expressing a protein of interest, localizing a protein in a cell, and designing a therapeutic agent for treating a disease or infection.

BACKGROUND

Several methods exist to monitor a target substance in a biological system, including monitoring activities inside a cell and intracellular processes. These methods utilize various reporter molecules and genes and other molecular tags and include, for example, the formation of fusion proteins with coding sequences for chloramphenicol acetyl transferase (CAT), gluceronidase (GUC), beta-galactosidase (bGAL) and luciferases (LUC). Many of these reporters and tags may be used as indicators of processes that would be hard to detect otherwise. Silhavy, T. J. & Beckwith, J. R. *Microbiol. Rev.* (49), 398 (1985); Gould, S. J. & Subramani, S. *Anal. Biochem.* (175), 5 (1998); and Stewart, G. S. A. B. & Williams, P. J. *Gen. Microbiol.* (138), 1289 (1992).

Many uses of these reporter genes have been described extensively in the prior art. There use, however, has been limited because they require extra manipulations. For example, the fixing of cell preparations or the addition of exogenous substrates or cofactors makes it difficult to incorporate the use of these reporters in highly automated assays. In contrast, the use of another reporter gene, the green fluorescent protein (GFP), is not limited by these restrictions but suffers from other disadvantages, such as background noise and the need for complex and expensive equipment for detection. Cormack, B. P., et al. *Gene*, 173(1):33–38 (1996); Kroes, S. J., et al., *Eur. J. Biochem.* 240(2), 342–351 (1996).

Furthermore, until recently, detection in automated assays was based on enzymatic or fluorimetric methods for reasons of sensitivity. As detection at the microscopic level has developed, however, it has become technically possible to use markers without amplification of the marker itself, or signal amplification. Thus, the development of novel reporter genes or markers that have none of the above limitations and disadvantages are desired.

SUMMARY OF THE INVENTION

To achieve these and other advantages, and in accordance with the purpose of the invention as embodied and broadly described herein, the present invention, in one aspect, provides a method of monitoring a target substance in a biological system comprising providing a biological system with a target substance that is labeled with an apo metal binding protein. Conditions are provided which permit the apo metal binding protein to emit a signal and the signal is observed or measured. The target substance is monitored based on the signal. The method of monitoring a comprise determining the location of the target substance and/or quantifying the amount of target substance in the biological system.

An another embodiment, the invention, using the method of monitoring a target substance described above, provides for a method of determining the cytotoxicity of a drug of interest. The target substance, a cell, is labeled with an apo metal binding protein and is exposed to the drug of interest. The cell is monitored and the cytotoxicity of the drug of interest is determined by whether the cell is influenced by the drug of interest.

The invention also provides for a method of labeling a protein of interest comprising fusing a protein of interest to an apo metal binding protein. In a further embodiment, the invention provides a method of labeling a cell of interest comprising introducing into the cell an apo metal binding protein or by binding to the membrane of the cell an apo metal binding protein.

The invention further provides a method for detecting a cell expressing a protein of interest comprising introducing into the cell a DNA molecule having a DNA sequence encoding the protein of interest and an additional DNA molecule having a DNA sequence encoding an apo metal binding protein. Conditions are then provided which permit expression of the apo metal binding protein and the protein of interest. Conditions are also provided which permit the apo metal binding protein to emit a signal. The cell expressing the protein of interest is detected by observing or measuring the signal of the apo metal binding protein.

In another embodiment, the invention provides a method for localizing a protein of interest in a cell comprising introducing into the cell a DNA molecule comprising a DNA sequence encoding the protein of interest, linked to an additional DNA sequence encoding an apo metal binding protein. The two sequences are linked such that the protein produced by the DNA molecule will have the protein of interest fused to the apo metal binding protein. Conditions are provided which permit expression of the fused protein. Conditions are also provided which permit the apo metal binding protein to emit a signal. The location of the fused protein, and thereby the location of the protein of interest in the cell, is determined by observing or measuring the signal.

The invention also provides a method of designing a therapeutic agent for treating a disease. A cell that is a target of the disease is labeled with the apo metal binding protein and conditions are provided which permit the protein to emit a signal. Whether the therapeutic agent is effective treating the disease is determined by monitoring the signal observed or measured from the cell.

In a further embodiment, the methods of the invention may be used to design a therapeutic agent for treating a virus or bacterial infection comprising labeling the virus or the bacteria with an apo metal binding protein. Conditions are provided which permit the apo metal binding protein to emit a signal and the signal is observed or measured. The effectiveness of the therapeutic agent for treating the virus or bacterial infection is determined by observing or measuring the signal from the virus or the bacteria.

The invention also contemplates a eucaryotic cell comprising a DNA sequence that encodes an apo metal binding protein. In one embodiment, the eucaryotic cell is an animal cell, the apo metal binding protein is a copper binding protein and the DNA sequence comprises the azu gene.

Additional objects and advantages of the invention will be set forth in part in the description that follows, and in part will be apparent from the description, or may be learned by practice of the invention. The objects and advantages of the invention will be realized and attained by means of the elements are combinations particularly pointed out in the appended claims.

It is to be understood that both the foregoing general description and the following detailed description are exemplary and explanatory only and are not restrictive of the invention as claimed.

BRIEF DESCRIPTION OF THE DRAWINGS

FIG. 1 depicts the primers used to amplify the azu gene from bacterial DNA by PCR; the 5' primers BCP-1C or BCP-2C, and the 3' primer BCP-1NC.

Figure 2:
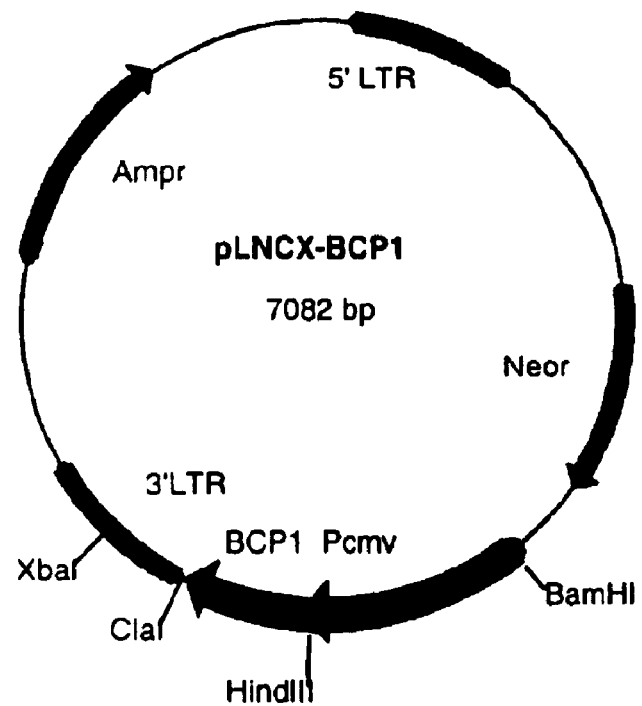
FIG. 2 is a map of the pLNCX-BCP1 vector: 5' MoMuLV LTR: 145–733; $\Psi^+$ (extended packaging signal): 803–1612; Neomycin resistance gene (Neo'): 1656–2450; Immediate early CMV promoter (Pcmv): 2800–3617; BCP1-gene: 3622–4701; 3' MoMuLV LTR: 4128–4720; Ampicillin resistance gene (B-lactamase, Amp'): 6023–6865.

The pLNCX-BCP1 was deposited at the Belgian Co-ordinated Collections of Micro-Organisms located at the University Gent-Laboratorium voor Moleculaire Biologie on Aug. 3, 2000, and the accession number is LMBP4156.

FIG. 3 depicts the western blots of cell lysates. The blots confirm the expression of azurin.

DETAILED DESCRIPTION OF THE INVENTION

Reference will now be made in detail to the presently preferred embodiments of the invention. The invention, in one aspect, provides a method of monitoring at least one target substance in a biological system comprising labeling a target substance in the biological system with an apo metal binding protein. Conditions are then provided which allow the apo metal binding protein to emit a signal and the signal may then be observed or measured. The signal may be used to monitor the target substance including, but not limited to, the location or position of the target substance within the biological system and/or quantity of the target substance in the biological system.

An apo metal binding protein, as define herein, is any protein or peptide that acquires a detectable color upon the binding of one or more metal ions or changes in color upon binding of a metal ion or an additional metal ion. The color obtained or the change in color observed may also vary with the oxidation state of the metal ion. In one embodiment, the invention utilizes this characteristic as a marker for the analysis of a biological process including, but not limited to, any process inside or outside cells, in in vitro assays or to observe cells or processes in tissues or in whole organisms. In a further embodiment, the apo metal binding protein includes groups or families of metal binding proteins that carry an intense color or color change upon binding with a metal.

Apo metal binding proteins acquire a detectable color or change in color upon binding of a metal ion as opposed to proteins that generate a color by an enzymatic reaction or proteins that contain a luminophore. Thus, apo metal binding proteins, which acquire an intrinsic, easily detectable color, provide a novel marker.

Apo metal binding proteins are a heterogeneous collection of proteins from various sources including blue copper proteins in bacteria and mammalian proteins like haemoglobulin, catalase and transferrin. The major advantage of the use of apo metal binding proteins as markers compared to the use of existing reporter genes or markers is the fact that they can be easily detected without the need for extra manipulations or the use of expensive and sophisticated equipment. As many of these proteins do not occur in mammalian cells they are perfect markers to introduce into such cells (e.g. in diagnostic assays).

To date, apo metal binding proteins have not been used as markers in analytical testing, diagnostic testing or screening for drugs. One patent (U.S. Pat. No. 5,210,019) describes the use of azurin, a blue copper protein, to detect pseudomonas bacteria. However these bacteria naturally express azurin, i.e., the protein was not introduced into the bacteria with the intention of using it as a marker of an internal or external process. Azurin is only used to detect the presence of the bacteria as such. Similarly, PCT application, WO 99/30730A1, discloses the use of the metal binding protease superoxide dismutase, however, there is no disclosure of the metal binding protein as a reporter molecule or marker.

In one embodiment, the apo metal binding protein may be a copper protein, a derivative or mutant of a copper protein or any protein or peptide sequence with the copper binding characteristics of a copper protein sequence as described below. In living cells, copper carries out several physiological functions in association with specific metabolic proteins, e.g. participation in electron transfer reactions, various enzymatic reactions and transport or storage of the metal itself. Copper proteins and more specifically, blue copper proteins, consist of a wide variety of proteins (families) normally with a color that can be changed into other colors depending on pH and/or mutations. Kroes, S. J., et al., *Eur. J. Biochem.* 240(2), 342–351 (1996) and E. Solomon, *Chemical Reviews*, 96(7), 2239–2314 (1996). Copper proteins may be classified according to their biological function, by copper centre type, by number of prosthetic centres and be sequence similarity.

Alternative to copper proteins, other apo metal proteins may include proteins linked to a transition metal like Co, Ni, Mn, Zn, Fe, or an alkali metal like Ca, Mg, Na, and K.

In one embodiment, the apo metal binding protein is at least one blue copper protein, or a derivative or mutant of a blue copper protein. According to the classification of copper proteins by their copper centre, the blue copper proteins form a distinct class. In this class, they can be divided into three groups: the small blue copper proteins (e.g. azurins, pseudo-azurins, plastocyanin family, and phytocyanin family), the blue oxidases (e.g. ascorbate oxidase, ceruloplasmin, and laccase) and nitrite reductase.

Blue copper proteins, also referred to as "type-1" copper proteins, include but are not limited to small proteins that bind a single copper atom and which are characterized by their very intense absorption in the region of 600 nm due to a charge transfer transition from a cysteine residue. Not to be limited as to theory, there is a relation between the EPR spectrum of the blue copper proteins, the relative intensity of the important peaks in the UV/VIS absorption spectrum, and the structure of the active site. Based on these observed parameters, the most widely observed blue copper proteins may be divided into four structural classes.

The first class consists of the classical blue copper proteins, with its most studied example plastocyanin. Here the cysteine and the two histidine residues form a plane with the Cu(II) atom lying slightly above. The $S_{Cys}$-Cu(II) distance is very short (±2.1 Å). Axial to this plane, the fourth residue methionine, is at a large distance (±2.9 Å). The overall structure of the active site is distorted tetrahedral or trigonal ($C_{3v}$).

A second group of blue copper proteins includes those proteins in which links with five residues are coordinated: the azurins. The additional bond is formed by a carbonyl oxygen which binds to copper at the side opposite to methionine. The methionine residue is at a slightly larger distance than in plastocyanin (±3.1 Å). The carbonyl group is at about 3.0 Å. The EPR spectrum of the proteins belonging to the first and second class are of the axial type and they only show one intense peak near 600 nm in the absorption spectrum.

A third class of blue copper proteins includes those proteins which have the same four coordinating links as in plastocyanin, but which are arranged in a more distorted conformation. The $S_{Cys}$-Cu(II) bond length increases simultaneously with the decrease of the $S_{Me1}$-Cu(II) bond length. The EPR spectrum is rhombic and there is an increase of the absorption region of 460 nm.

A fourth class of blue copper proteins is formed by those proteins that have an axial link with a residue that is different from methionine.

Although there is an appreciable amount of divergence in the sequence of the blue copper proteins, the copper ligand sites for many of the proteins are conserved and show the following pattern: [GA]-x(0,2)-[YSA]-x(0,1)-[VFY]-x—C—x(1,2)-[PG]-x(0,1)—H—x(2,4)-[MQ]. See http://bess.u-strasbg.fr/BioInfo/Prosite/00174.pdoc. A special distorted trigonal planar arrangement of two histidine ligands and one cysteine ligand around the copper gives rise to the very peculiar electronic properties of the metal site: and intense blue color, which is about 100 times more intense than most inorganic copper complexes (Cys-S-Cu charge transfer), axial EPR-spectra with small hyperfine coupling constants and high redox potentials. In one embodiment, the apo metal binding protein for use in the practice of the invention is a blue copper protein with these characteristics.

The most well known members of this class of proteins are the plant chloroplastic plastocyanins, which exchange electrons with cytochrome c6, and the distantly related bacterial azurins, which exchange electrons with cytochrome 551. Other blue copper proteins include, but are not limited to, amicyanin from bacteria such as methylobacterium extorquens or thiobacillus versutus that can grow an methylamine; auracyanins A and B from chloroflexus aurantiacus; blue copper protein from alcaligenes faecalis; cupredoxin (CPC) from cucumber peelings; cusacyanin (basic blue protein, plantacyanin, CBP) from cucumber; halocyanin from natrobacterium pharonis, a membrane associated copper-binding protein; pseudoazurin from pseudomonas; rusticyanin from thiobacillus ferrooxidans; stellacyanin from the Japanese lacquer tree; umecyanin from horseradish roots; and allergen Ra3 from ragweed. Garret T. P. J., et al., *J. Biol. Chem.* 259:2822–2825(1984); Ryden L. G., & Hunt L. T., *J. Mol. Evol.* 36:41–66(1993); McManus J. D., et al., *J. Biol. Chem.* 267:6531–6540(1992); Mann K., et al., *FEBS Lett.* 314:220–223(1992); Mattar S., et al., *J. Biol. Chem.* 269:14939–14945(1994); Yano T., et al., *FEBS Lett.* 288:159–162(1991).

The signal emitted by an apo metal binding protein may be any change or acquisition of color or change in the intensity of color. Color, as used herein, is defined as any chromatic signal. In one embodiment, the color observed or detected is in the visible or ultraviolet wavelength range. Color as defined herein may also be a fluorescent or luminescent signal. The signal may be observed or measured by any means known in the art including, but not limited to, visible detection by the naked eye, a microscope, photon tube, or diode. In one embodiment, the frequency, duration, intensity, and/or localization of the signal is measured or observed at a single point in time or as a function of time.

As defined herein, a biological system may be any in vivo or in vitro biological or biochemical system including but not limited to any cell or cell culture, virus, bacteria, plant, or animal or any part or simulated system thereof. In the practice of the invention, the target substance may be chosen from any cell, such as bacterial, fungal, plant or animal cell, any tissue, any virus, or any protein. Suitable animal sells includes, but are not limited to Vero cells, HeLa cells, Cos cells, CVl cells and various primary mammalian cells. In an embodiment, the bacterial cells is *Escherichia coli*. The target substance may also be a drug or therapeutic treatment that is labelled in order to follow its activity or function in vivo or in vitro. In one embodiment, the apo metal binding protein is linked, e.g., covalent or ionic bond, to a tissue, cell, and/or a protein, or a fusion protein is prepared between one or more proteins of interest and one or more apo metal binding proteins.

A cell may also be labelled by introducing an apo metal binding protein into the cell or by transfecting the cell with a DNA molecule encoding an apo metal binding protein. An apo metal binding protein may also be bound or anchored to the membrane of a cell either inside or outside of the cell wall. The apo metal binding protein may be provided to a cell, tissue or protein of interest in vivo or in vitro.

Also within the practice of the invention is a eucaryotic cell comprising a DNA sequence encoding an apo metal binding protein, and in one embodiment a copper binding protein. The eucaryotic cell may be an animal cell and in one embodiment, the DNA sequence comprises the azu gene.

In one embodiment the apo metal binding protein may be used as reporter gene. The reporter gene may be inserted into a cell and the cell may comprise a DNA molecule having a regulatory element from a gene, other than a gene encoding an apo metal binding protein operatively linked to a DNA sequence encoding the apo metal binding protein. As used herein, "a regulatory element" from a gene is the DNA sequence which is necessary for the expression of the gene. In this invention, the term "operatively linked" means that following such a link the regulatory element can direct the expression of the linked DNA sequence. A gene encoding an apo metal binding protein includes DNA molecules coding for polypeptide analogs, fragments or derivatives or antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one ore more amino acid residues is added to a terminal or medial portion of the polypeptides) and which share some or all properties of naturally-occurring forms.

These DNA molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

In one embodiment, the apo metal binding proteins could be linked to a promotor that by itself is responsive to an intracellular process. Any influence (e.g. by a drug added to the cell) on that process would affect the expression rate of the metal binding protein and hence could be monitored by measuring the intensity of the color of the cell.

One of ordinary skill in the art will be able to determine the conditions which must be provided in order to permit an apo metal binding protein to emit a signal depending on the apo metal binding protein chosen and the application envisaged. The proper conditions may include, but are not limited to, varying pH, ionic strength, intracellular redox potential, providing a metal to bind to the apo metal binding protein, and altering the charge of the metal.

For example, to provide the conditions which permit azurin to emit a signal, e.g., blue color, two conditions should be fulfilled: (1) azurin has to bind copper either before or after labeling the target substance, and (2) the protein has to be in an oxidized state. Furthermore, these conditions have to be compatible with the in vivo or culturing conditions of the biological system. Free $Cu^{2+}$, for example, is toxic to the cells, even in relatively low concentrations.

Azurin binds copper with high affinity (the binding of copper is thermodynamically favored with the binding energy of Cu (II) exceeding those of other transition ions), and the resulting copper-protein complex is very stable. Therefore low, non-toxic, amounts of $Cu^{2+}$ in the medium (in a range of 0,5 to 1 $\mu M$) should allow irreversible binding of the metal to azurin. In one embodiment, the copper-transport within a biological system may occur by trafficking proteins, which take the $Cu^{2+}$ to different copper containing oxidases in the vesicular systems.

Not to be limited as to theory, the intense blue color of azurin is a property of the oxidized Cu(II) form, that possesses a strong visible absorption band at 628 nm ($\epsilon=5700$ $M^{-1}$ $cm^{-1}$), while the Cu(I) form is colorless. The oxidized azurin is the most stable form, but the reduction potential of the Cu-complexes is strongly influenced by the medium and ionic strength, and the blue color of the Cu(II) complex fades with decreasing pH. Thus, in one embodiment, a change in medium or ionic strength of the medium may provide the condition that permits the apo metal binding protein to emit a signal.

In a further embodiment, the physiologic pH of the cell cytoplasm allows formation of the functional protein. However, since the reduction potential of the cell environment however is rather low, therefore favoring the colorless Cu(I) form, in one embodiment, a cell is lysed at the endpoint of the assay for detection of the blue color of the expressed azurin in a lysisbuffer with compatible pH, copper concentration, and reduction potential.

In another embodiment, one may target the expressed apo metal binding protein to specific "oxidative" organelles like mitochondria, post-Golgi vesicles, and peroxisomes. According to the biological role of zaurin, for example, the mitochondria are the appropriate organelles for expression of the protein. Azurin belongs to a family of proteins which function in the respiratory chains of denitrifying bacteria and plants as electron-transfer agents. Their role is to transport electrons between different oxidases (e.g. cytochrome c and cytochrome oxidase, ATPases). The targeting of the proteins to the mitochondria can easily be accomplisehd by placing a mitochondrial targeting signal in front of the azu gene coding sequence.

Targeting of azurin to the mitochondria has an additional advantage on the concentration of the expressed protein. Although expression of the pLNCX-BCP1/2 constructs is induced by the strong constitutive CMV-promoter, the amount of azurin in some systems may be insufficient for efficient detection of the blue color, because there is no enzymatic amplification of the signal (=blue color). Targeting the proteins to the mitochondria concentrates the blue color which should allow a more accurate detection. The protein yield can also be enhanced by placing a translational enhancer directly upstream of the coding sequence of azurin. In that way up to five-fold higher levels of expression can be achieved. As a result of targeting and enhanced expression, the mitochondrial blue "pixels" should be easily detected and measured with, for example, an electron microscope, a confocal microscope, a color camera, or the Tibotec multi-sampling microscope (Tibotec) as described in U.S. patent application Ser. No. 09/521,618.

There are countless applications in which the methods and compositions of the present invention may be applied. For example, in one embodiment, the invention provides for a method for detecting at least one cell expressing a protein of interest. A DNA molecule having a DNA sequence encoding one or more protein(s) of interest and an additional DNA molecule having a DNA sequence encoding one or more apo metal binding protein(s) may be inserted into the cell. By providing conditions which permit the apo metal binding protein to emit a signal, one may detect the cell expressing the protein of interest by observing or measuring the signal of apo metal binding protein. The DNA molecule and the additional DNA molecule may be linked.

In another embodiment, the invention provides a method for localizing at least one protein of interest in a cell. Here, introduced into the cell is a DNA molecule comprising a DNA sequence encoding the at least one protein of interest, linked to an additional DNA sequence encoding an apo metal binding protein. The sequences are linked such that the protein produced by the DNA molecule will have the at least one protein of interest fused to the apo metal binding protein. The location of the fused protein may be determined from the signal of the expressed fusion protein, thereby localizing the protein of interest in the cell.

The invention includes the use of the these proteins or peptides in drug discovery technologies and diagnostic testing. In one embodiment, the invention provides for a drug or a treatment discovered, identified or designed using the methods described herein.

The methods of the invention are especially applicable in high throughput testing or evaluation devices. The invention could also be used in high throughput screening for drugs. In this area the speed of the screening is considered as one of the most important bottlenecks in the process of drug discovery. A simplification of the detection of the reporter or tag is one way to speed up the screening process. The apo metal binding proteins are ideal for this purpose. There would be no need for extra manipulations for detection and thus could be used in homogenous assays, making them amenable to automation. The fact that there's no need for sophisticated and expensive detection equipment is another important direct advantage It is within the practice of the invention to prepare a sample rack or solid support made up of numerous reaction wells, such that each reaction remains isolated form one another. Simultaneous transfer of one or more reagents to the reaction wells may then be achieved by one of the many techniques used in the art of high throughput analysis.

One or more of the contents of each of the reaction wells may be varied. For example, in one embodiment, each reaction well contains the same biological system and target substance labeled with an apo metal binding protein. However, a drug is then added to each reaction well. The reaction wells may form an array or may employ another means of identifying or addressing each compartment. The activity of each reaction well may then be automatically determined from the amount of signal from an apo metal binding protein detected, and recorded. Other embodiments include, but are not limited to varying the concentration of one or more of the components.

There are numerous methods for handling high throughput. i.e., analyzing a large number of samples in a relatively short period of time. Any method of high throughput analysis available may be applied to the methods of the invention.

Examples include, but are not limited to: U.S. Pat. No. 5,985,215 of Sakazume et al., entitled *Analyzing Apparatus Having a Function Pipette Samples*; U.S. Pat. No. 6,046,056 to Parce et al., entitled *High Throughput Screening Assay Systems in Microscale Fluidic Devices*; WO 00/14540 of Pauwels et al., entitled *Method for the Rapid Screening of Analytes*; WO 99/30154 of Beutel et al., entitled *Continuous Format High Throughput Screening*; and WO 99/67639 of Wada et al., entitled *High Throughput Methods, Systems and Apparatus for Performing Cell Based Screening Assays*, the disclosures of which are herein incorporated by reference in their entirety.

In a specific embodiment, apo metal binding proteins may be used as reporter in diagnostic testing, such as drug sensitivity analysis, as performed according to WO97/27480. In one embodiment, the invention provides a method of designing a therapeutic agent for treating a disease comprising labeling at least one cell that is a target of the disease with an apo metal binding protein. Whether the therapeutic agent is effective treating the disease is determined by monitoring the signal observed or measured from the apo metal binding protein and thus the cell.

The invention also provides a method of designing a therapeutic agent for treating a virus or bacterial infection. The virus or the bacteria is labeled with an apo metal binding protein and conditions are provided which permit the apo metal binding protein to emit a signal. Whether the therapeutic agent is effective treating the virus or bacterial infection is determined by monitoring the signal observed or measured from the virus.

In one embodiment, the virus is the HIV virus and the apo metal binding proteins are used for the screening of drugs that are effective against HIV. For example, the gene coding for this protein could be operatively linked to a constitutively active promotor of a $CD4^+$ cell. If the drug is inactive against the virus, the addition of the drug and the HIV virus to a $CD4^+$ cell will kill that cell because the virus is able to enter and kill the cell. The cell will express the metal binding protein no more and will loose its color. If it is a drug active against HIV, the virus can't kill the cell and the cell will keep its color. The cytotoxicity of drugs could also be determined by the use of these novel markers. In this case, the gene coding for the apo metal binding protein could be operatively linked to a constitutively active promoter and introduced in a cell. Living cells, which are not influenced by a drug would be detected as they continue to support gene expression and thus express the metal binding protein giving the cell an intense color. If a drug is toxic to the cell, there will be no more expression of the marker and the color of the cell would disappear.

In addition one could envision the use of an apo metal binding protein or related peptide in almost any application in which a green fluorescent protein (GFP) (or related mutants thereof) is used. Many uses of GFP are disclosed/covered by U.S. Pat. No. 5,491,084. One example is the use of (modified) GFP in a farnesyl-transferase assay we described recently (PCT/EP00/04923 bs PCT/EP/004919) in which a colored metal binding protein would be incorporated in a fusion protein containing a cleavable site (such as DVED for caspases) together with Ras sequences that target the entire fusion protein to the plasma membrane. Any action of a protease, such as caspase, would cause a detectable redistribution of the metal binding protein within the cell.

An apo metal binding protein may also replace currently used reporters in diagnostic testing such as the anti Virogram™ procedure as disclosed in WO97/27480.

The invention also provides for a kit. The kit may be used for any of the methods described herein. In one embodiment, the kit may be used to monitor at least one target substance in a biological system. The kit of the invention may comprise an apo metal binding protein and/or a DNA sequence encoding an apo metal binding. The kit may further comprise a plasmid for delivering the DNA sequence encoding an apo metal binding protein to a cell. In another embodiment, a kit comprises a eucaryotic cell comprising a DNA sequence encoding an apo metal binding protein.

EXAMPLES

Example 1

Construction of pLNCX-BCP1 and pLNCX-BCP2

The bacteria *Achromobacter xylosoxidans* subsp. *dentrificans* (or *Alcaligenes dentrificans*) was purchased from the ATCC (ATCC number 15173, NCTC 8582). The gene azu coding for azurin was PCR-amplified from bacterial DNA and cloned into a mammalian expression vector. The azu gene codes for a pre-protein in which the mature azurin (130 AA) is preceded by a 19-AA signal pepetide. This peptide probably serves the purpose of translocating the protein across the periplasmic membrane. The complete protein (with signal peptide) was cloned in order not to have difficulties with correct protein folding. In a second construct a secretion signal (=lg ϵ-leader sequence) was placed before the gene, to allow secretion into the medium.

The azu gene was cloned into the retroviral vector pLNCX (Clontech). This vector, derived from Moloney murine leukemia virus (MoMuLV), is designed for retroviral gene delivery and expression. It contains a neomycin resistance (Neo') gene controlled by 5' viral LTR (5' LTR) for antibiotic selection in eukaryotic cells and a cloning site (Hind III, Hpal and Clal) downstream from a cytomegalovirus (Pcmv) immediate early promotor. The $\Psi^+$ sequence is an extended viral packaging signal required for the viral vector transcript to be packaged in virions. pLNCX does not contain the viral structural genes (gag-pol and env) necessary for particle formation and replication, however, they can be provided in trans in packaging cell lines stably expressing these genes.

The azu gene was amplified from bacterial DNA by PCR using the 5' primers BCP-1C (SEQ ID:1) or BCP-2 (SEQ ID:3), and the 3' primer BCP-1NC (SEQ ID: 2) (FIG. 1). The 5' primers are designed containing a translation initiation (Kozak) sequence before the initiating ATG codon. The primer BCP-2-C includes the Ig ϵ-leader sequence for secretion of BCP into the medium. The 3' primers include the native stop codon of the protein. The primers also contain a restriction site (HindII for the 5' primers and EcoRI for the 3' primers) that allows an easy subcloning of the azu gene.

The PCR product was, after restriction with HindIII, cloned into the HindIII-Hpal site of pLNCX (FIG. 2).

Example 2

Transfection and Detection of Azurin in Eukaryotic Cells

The protein azurin is a blue copper protein that is characterized by an intense absorption near 600 nM causing a blue color when $Cu^{2+}$ is bound to the protein. The protein is expressed by different strains of bacteria. The blue colored protein was expressed in eukaryotic cells, and used as an alternative for different reporter systems (β-gal, GFP, . . . ) in cell-based assays. The experiment showed that constitutive expression and detection of the portion could be used as a viability marker.

293T cells, T-antigen transformed human embryonic kidney cells, were transiently transflected with the constructs pLNXC-BCP1 or pLNCX-BCP2 using Effectene transfection reagent (Qiagen). SDS-PAGE (15%) followed by Western blotting of the cell lysates confirmed expression of azurin by both constructs (FIG. 3).

The azurin was detected in cell lysates (Cell lysates ($10^6$ cells/sample)) with polyclonal antibody anti A. denitrificans azurin (Leiden Institute of chemistry, Gorlaeus laboratories). The Western blots shown in FIG. 3 may be interpreted as follows:

| | |
|---|---|
| Lane 1: Biorad Prestained Marker Broadrange | Lane 2: 15 μl sample |
| Lane 3: 10 μl sample | Lane 4: 7.5 μl sample |
| Lane 5: 5 μl sample | Lane 6: 2.5 μl sample |
| Lane 7: negative control (non-transfected cells) | Lane 8: empty |
| | Lane 10: *P. aeruginosa* azurine |
| Lane 9: *A. denitrificans* azurine | |

All references, patents, and patent applications cited herein are incorporated by reference in their entirety.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A method of monitoring at least one cell or tissue in a biological system comprising:
    a) providing said biological system comprising said at least one cell or tissue;
    b) labeling said at least one cell or tissue with at least one apo metal binding protein;
    c) providing conditions which permit said at least one apo metal binding protein to emit a signal;
    d) observing or measuring the signal; and
    e) monitoring said at least one cell or tissue based on the signal observed or measured;
    wherein the cell or tissue is labeled by introducing into said cell or tissue a DNA molecule encoding said at least one apo metal binding protein.

2. A method of monitoring at least one cell or tissue in a biological system comprising:
    a) providing said biological system comprising said at least one cell or tissue;
    b) labeling said at least one cell or tissue with at least one apo metal binding protein;
    c) providing conditions which permit said at least one apo metal binding protein to emit a signal;
    d) observing or measuring the signal; and
    e) monitoring said at least one cell or tissue based on the signal observed or measured;

SEQUENCE LISTING

<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 1
gacagaagct tcgccaccat gctggcaaaa gccac         35

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 2
gacagaattc agttgctcag cttgagcgtg         30

<210> SEQ ID NO 3
<211> LENGTH: 98
<212> TYPE: DNA
<213> ORGANISM: Artificial Sequence
<220> FEATURE:
<223> OTHER INFORMATION: Description of Artificial Sequence: primer

<400> SEQUENCE: 3
gacagaagct tcgccaccat ggagacagac acactcctgc tatgggtact gctgctctgg         60
gttccaggtt ccactggtga catgctggca aaagccac         98 wherein the cell or tissue is labeled by introducing into said cell or tissue DNA molecule encoding a fusion protein comprising at least one apo metal binding protein.

3. A method of monitoring at least one cell or tissue in a biological system comprising:
   a) providing said biological system comprising said at least one cell or tissue;
   b) labeling said at least one cell or tissue with at least one apo metal binding protein;
   c) providing conditions which permit said at least one apo metal binding protein to emit a signal;
   d) observing or measuring the signal; and
   e) monitoring said at least one cell or tissue based on the signal observed or measured;
   wherein said conditions which permit said at least one apo metal binding protein to emit a signal comprise providing at least one metal which binds to said at least one apo metal binding protein; wherein said apo metal binding protein is a blue copper protein chosen from azurin, pseudo-azurin, a plastocyanin, and a phytocyanin.

4. A method of monitoring at least one target substance in a biological system comprising:
   a) providing said biological system comprising said at least one target substance, wherein said at least one target substance is a cell that is labeled by transfecting said cell with a DNA molecule encoding said at least one apo metal binding protein; b) providing conditions which permit said at least one apo metal binding protein to emit a signal;
   c) observing or measuring the signal; and
   d) monitoring said at least one target substance based on the signal observed or measured.

5. The method of claim 4, wherein said cell is labeled by introducing into said cell a DNA molecule encoding a fusion protein which has at least one apo metal binding protein.

6. A method of monitoring at least one target substance in a biological system comprising:
   a) providing said biological system comprising said at least one target substance;
   b) labeling said at least one target substance with at least one apo metal binding protein, wherein said apo metal binding protein is a blue copper protein, and said blue copper protein is chosen from azurin, pseudo-azurin, a plastocyanin, and a phytocyanin;
   c) providing conditions which permit said at least one apo metal binding protein to emit a signal, wherein said conditions which permit said at least one apo metal binding protein to emit a signal comprise providing at least one metal which binds to said at least one apo metal binding protein;
   d) observing or measuring the signal; and
   e) monitoring said at least one target substance based on the signal observed or measured.

* * * * *